(12) United States Patent
Slate et al.

(10) Patent No.: US 7,618,396 B2
(45) Date of Patent: Nov. 17, 2009

(54) INJECTION SYSTEM WITH HIDDEN NEEDLES

(75) Inventors: John B. Slate, San Diego, CA (US); Andrew C. Barnes, San Diego, CA (US); Corey M. Magers, San Diego, CA (US)

(73) Assignee: Avant Medical Corp., San Diego, CA (US)

( * ) Notice: Subject to any disclaimer, the term of this patent is extended or adjusted under 35 U.S.C. 154(b) by 0 days.

(21) Appl. No.: 11/463,529

(22) Filed: Aug. 9, 2006

(65) Prior Publication Data
US 2008/0039795 A1 Feb. 14, 2008

(51) Int. Cl.
*A61M 5/20* (2006.01)
*A61M 5/00* (2006.01)

(52) U.S. Cl. ...................................... 604/136; 604/187

(58) Field of Classification Search ................ 604/130, 604/72, 181, 68, 183, 136, 135–139, 62, 604/65, 184, 194–195, 201, 232, 187; 600/432; 206/364, 380, 382; 29/777
See application file for complete search history.

(56) References Cited

U.S. PATENT DOCUMENTS

| | | | | |
|---|---|---|---|---|
| 857,739 A * | 6/1907 | Kennerly | ................ | 604/183 |
| 1,539,637 A * | 5/1925 | Bronner | ................ | 433/81 |
| 2,645,224 A * | 7/1953 | Beebe | ................ | 604/183 |
| 2,691,372 A * | 10/1954 | Lores | ................ | 604/201 |
| 2,888,924 A * | 6/1959 | Dunmire | ................ | 604/196 |
| 3,380,449 A * | 4/1968 | Sarnoff | ................ | 604/200 |
| 3,391,695 A * | 7/1968 | Sarnoff | ................ | 604/200 |
| 3,930,761 A * | 1/1976 | Barraclough | ................ | 417/476 |
| 4,004,565 A * | 1/1977 | Fischer et al. | ................ | 124/45 |
| 4,164,929 A * | 8/1979 | Liepins et al. | ................ | 124/76 |
| 4,223,674 A * | 9/1980 | Fluent et al. | ................ | 604/507 |
| 4,241,728 A * | 12/1980 | Mirell | ................ | 600/5 |
| 4,291,695 A * | 9/1981 | Bekkering et al. | ................ | 604/200 |
| 4,394,863 A * | 7/1983 | Bartner | ................ | 604/90 |
| 4,447,223 A * | 5/1984 | Kaye et al. | ................ | 604/61 |
| 4,503,856 A * | 3/1985 | Cornell et al. | ................ | 606/182 |
| 4,518,384 A * | 5/1985 | Tarello et al. | ................ | 604/61 |
| 4,790,823 A * | 12/1988 | Charton et al. | ................ | 604/136 |
| 4,795,433 A * | 1/1989 | Sarnoff | ................ | 604/134 |
| 4,813,940 A | 3/1989 | Parry | | |
| 5,080,648 A * | 1/1992 | D'Antonio | ................ | 604/72 |
| 5,085,642 A * | 2/1992 | Sarnoff et al. | ................ | 604/134 |
| 5,102,393 A * | 4/1992 | Sarnoff et al. | ................ | 604/136 |
| 5,104,384 A | 4/1992 | Parry | | |
| 5,135,493 A * | 8/1992 | Peschke | ................ | 604/61 |
| 5,267,972 A | 12/1993 | Anderson | | |
| 5,292,314 A | 3/1994 | D'Alessio et al. | | |
| 5,295,965 A * | 3/1994 | Wilmot | ................ | 604/136 |
| 5,318,522 A * | 6/1994 | D'Antonio | ................ | 604/72 |
| 5,370,611 A * | 12/1994 | Niezink et al. | ................ | 604/62 |
| 5,376,080 A | 12/1994 | Petrussa | | |
| 5,389,085 A | 2/1995 | D'Alessio et al. | | |
| 5,403,286 A | 4/1995 | Lockwood, Jr. | | |
| 5,520,639 A | 5/1996 | Peterson et al. | | |
| 5,522,374 A * | 6/1996 | Clayton | ................ | 124/59 |
| 5,522,797 A * | 6/1996 | Grimm | ................ | 604/61 |

(Continued)

*Primary Examiner*—Kevin C Sirmons
*Assistant Examiner*—Michael J Anderson
(74) *Attorney, Agent, or Firm*—Nydegger & Associates

(57) ABSTRACT

An auto-injector confines all functional components inside an enclosed housing, to keep its needle out-of-sight, at all times. Within the housing, a needle holder positions a needle at a location. A drive mechanism then simultaneously engages the needle with a fluid source and accelerates it with a predetermined momentum for insertion into a patient. After fluid delivery, the withdrawn needle is moved to storage within the housing for subsequent disposal.

22 Claims, 3 Drawing Sheets

U.S. PATENT DOCUMENTS

| | | | |
|---|---|---|---|
| 5,533,978 A * | 7/1996 | Teirstein | 604/183 |
| 5,569,190 A * | 10/1996 | D'Antonio | 604/72 |
| 5,817,054 A * | 10/1998 | Grimm | 604/62 |
| 5,829,589 A * | 11/1998 | Nguyen et al. | 206/366 |
| 5,993,412 A | 11/1999 | Deily et al. | |
| 6,010,485 A * | 1/2000 | Buch-Rasmussen et al. | 604/191 |
| 6,371,939 B2 * | 4/2002 | Bergens et al. | 604/156 |
| 6,406,456 B1 * | 6/2002 | Slate et al. | 604/68 |
| 6,599,272 B1 * | 7/2003 | Hjertman et al. | 604/209 |
| 6,605,058 B1 * | 8/2003 | Wich | 604/117 |
| 6,641,565 B1 * | 11/2003 | Lavi et al. | 604/183 |
| 6,645,169 B1 * | 11/2003 | Slate et al. | 604/68 |
| 6,652,483 B2 * | 11/2003 | Slate et al. | 604/68 |
| 6,669,664 B2 * | 12/2003 | Slate et al. | 604/68 |
| 6,689,108 B2 * | 2/2004 | Lavi et al. | 604/211 |
| 6,893,420 B2 * | 5/2005 | Arnisolle | 604/135 |
| RE39,014 E * | 3/2006 | Hansen | 424/423 |
| 7,207,974 B2 * | 4/2007 | Safabash et al. | 604/136 |
| 7,217,253 B2 * | 5/2007 | Slate et al. | 604/68 |
| 7,229,458 B2 * | 6/2007 | Boecker et al. | 606/181 |
| 2002/0007142 A1 * | 1/2002 | Hjertman et al. | 604/38 |
| 2002/0055707 A1 * | 5/2002 | Slate et al. | 604/72 |
| 2002/0108614 A1 * | 8/2002 | Schultz | 128/207.14 |
| 2002/0188419 A1 * | 12/2002 | Slate et al. | 702/176 |
| 2003/0050592 A1 * | 3/2003 | Slate et al. | 604/35 |
| 2003/0105430 A1 * | 6/2003 | Lavi et al. | 604/136 |
| 2004/0059286 A1 * | 3/2004 | Slate et al. | 604/68 |
| 2004/0267160 A9 * | 12/2004 | Perez | 600/583 |
| 2005/0020969 A1 * | 1/2005 | Slate et al. | 604/65 |
| 2005/0065472 A1 * | 3/2005 | Cindrich et al. | 604/134 |
| 2006/0069351 A9 * | 3/2006 | Safabash et al. | 604/136 |
| 2006/0173408 A1 * | 8/2006 | Wyrick | 604/110 |
| 2006/0178634 A1 * | 8/2006 | Wyrick | 604/157 |
| 2007/0017533 A1 * | 1/2007 | Wyrick | 128/898 |
| 2007/0142776 A9 * | 6/2007 | Kovelman et al. | 604/136 |

* cited by examiner

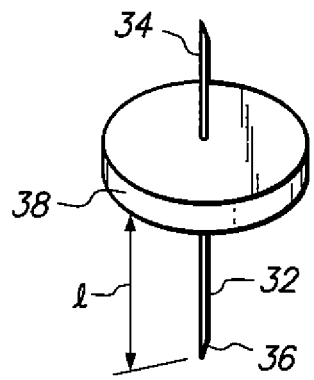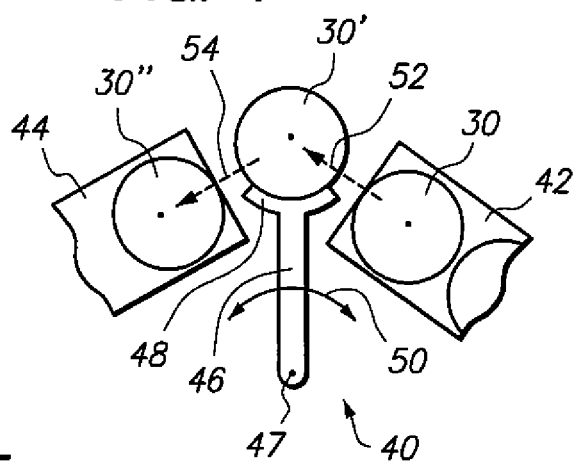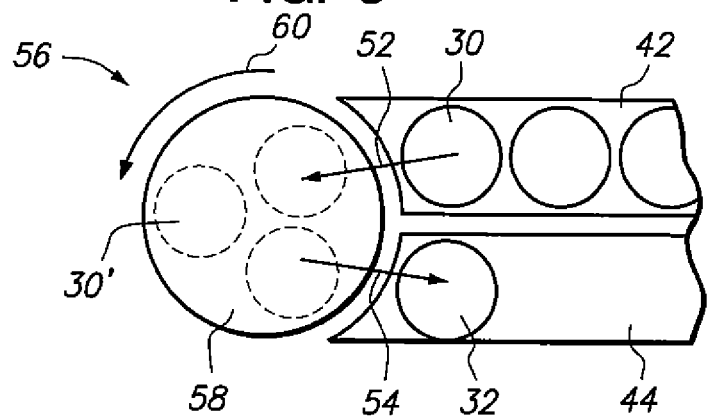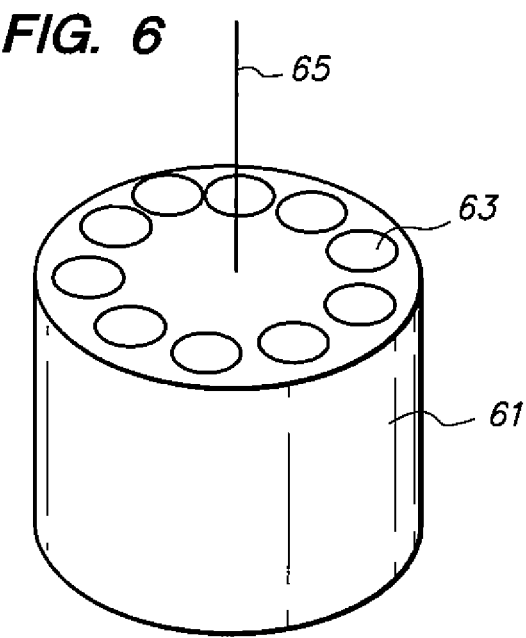

INJECTION SYSTEM WITH HIDDEN NEEDLES

FIELD OF THE INVENTION

The present invention pertains generally to systems and devices for using a needle to inject fluid medicaments into the body of a patient. More particularly, the present invention pertains to auto-injectors that can be used by a caregiver, or used individually by a patient to self-administer a fluid medicament. The present invention is particularly, but not exclusively, useful as a system and method for conveniently self-administering an injection without ever subjecting the user to a visual confrontation with the needle.

BACKGROUND OF THE INVENTION

Injectable drugs are necessary for numerous medical reasons, and they are typically used in a wide variety of applications. Consequently, various types of drug delivery systems have been developed to meet the many diverse needs of particular medical procedures. With any injectable drug delivery system, however, both physical and psychological implications are involved. Both are important, and both deserve consideration.

In general, all injectable drug delivery systems require some mechanical device or system that will drive or force a liquid into the body of a person or animal. Typically, this can be done in either of two ways. One way is to use a hypodermic needle. The other requires the use of a so-called needleless injector that relies on a liquid jet to create a hole in the skin. The liquid (i.e. fluid medicament) is then forced through the hole and into the body. Although needleless injectors are particularly efficacious for subcutaneous injections, they typically require excessive power to achieve the depth normally required for many intramuscular injections. With the above in mind, the focus here is on drug delivery systems that require the use of a hypodermic needle.

The physical implications that are involved when a hypodermic needle is used with an injectable drug delivery system pertain primarily to the needle itself. The length, the diameter and the needlepoint characteristics of a hypodermic needle are all obvious considerations in this context. Collectively, during the development of an injectable drug delivery system, these considerations must be engineered to: 1) establish the proper depth of an injection; 2) avoid a tissue compression, that will either cause a deep injection or result in needlepoint deformation due to bone contact (i.e. "fish hook"); 3) minimize the dangers of handling needles; and 4) allow for effective insertion of the needle into the body. An improper engineering of some, or all, of these considerations may affect drug absorption rates or cause pain. Apart from these considerations, however, the psychological implications that result from using a hypodermic needle may be even more profound. This is particularly so when the fluid medicament is to be self-administered.

Like the physical implications noted above, the psychological implications that are involved when a hypodermic needle is used with an injectable drug delivery system pertain primarily to the needle. Needle anxiety is real. For instance, many patients have a natural aversion to even the sight of a needle. Further, this aversion frequently evokes fear of injection site reactions (e.g. pain and bruising) that may, or may not, be real. And, when the injection needs to be self-administered, the task itself will often cause a hesitation or paralysis on the part of the user that prevents accomplishing a proper injection. In this context, it is known that "needle anxiety" has caused some patients to unnecessarily delay the beginning of a therapy regime for extended periods of time (e.g. several years).

Several attempts have been made to overcome many of the aforementioned implications that are associated with injectable drug delivery systems. For one, there have been efforts to provide so-called auto-injectors that will automatically drive a needle attached to a syringe into the skin to perform an injection. Typically, this is a push-button operation that is accomplished without any direct manipulation of the injectors drive mechanism. Nevertheless, prior to use, auto-injectors invariably involve many complicated steps for set-up. And, after use, they require special disposal procedures for the needle. Unfortunately, these operations typically expose the user to a visual contact with a needle that can trigger "needle anxiety." Also, injections with an auto-injector can be perceived to be more painful than a regular syringe injection due to the auto-injector's response to the drive mechanism actuation. Further, auto-injectors are typically not configured to conveniently provide for the sequence of multi-dose injections that may be required for many treatment regimes.

In light of the above, it is an object of the present invention to provide an auto-injector that is convenient to use and that requires minimal manipulation before, during, and after an injection. Another object of the present invention is to provide an auto-injector that overcomes needle anxiety by keeping the needle(s) hidden from patient-view at all times. Still another object of the present invention is to provide an auto-injector that conveniently uses a "clip" or "magazine" of sterile needles to eliminate operating steps, and to allow a patient to follow a multi-dose treatment regime wherein a new sterile needle is automatically provided for each injection. Yet another object of the present invention is to provide an auto-injector that automatically captures used needles and stores them out-of-sight for a subsequent safe and simple disposal with regular trash. Another object of the present invention is to provide an auto-injector that is easy to use, is relatively simple to manufacture, and is comparatively cost effective and provides a comfortable injection.

SUMMARY OF THE INVENTION

In accordance with the present invention, an auto-injector is provided that is effectively self-contained inside the interior of a housing. The intent here is to keep all operational components of the auto-injector, and most importantly its needle, out-of-sight and hidden from the view of the user. As envisioned for the present invention, this concealment of the needle is accomplished before, during and after an injection. To do this, the needles that are to be used with the auto-injector can be preloaded and supplied inside a casement (magazine, drum, etc.) for insertion into or for attachment to the auto-injector. The needle casement can then be used, and subsequently discarded as a unit without the user ever seeing or handling any of the needles. Some additional benefits of the present invention are also noteworthy. Specifically, with a completely enclosed operation, there is increased safety when using the auto-injector of the present invention. Moreover, each needle is used only once. This fact, alone, helps prevent contamination and insures that the structural integrity and lubricity of each needle are maintained until there is an actual use of the needle.

Structurally, the auto-injector of the present invention is characterized by an external housing that encloses many operational components in its interior. In particular, a replaceable fluid reservoir (e.g. cartridge) can be mounted on the housing to provide a fluid medicament for injections into the user. As intended for the present invention, the fluid reservoir may contain either a single dose of the desired fluid medicament, or multiple doses of the medicament. Also mounted onto the housing is a magazine, or clip, that holds a plurality of sterile needles. Further, a drive mechanism for inserting a needle into the patient is mounted in the interior of the housing. These components then interact with each other inside the housing via a connector and a needle holder. Specifically, the needle holder is used to operationally position the needle for connection with the connector, and the connector is used to connect the needle in fluid communication with the fluid reservoir. The needle/connector combination then cooperates with the drive mechanism to insert the needle into the user.

As envisioned for the present invention, the needle will typically be an elongated hypodermic needle that has both a sharp distal end and a sharp proximal end. Additionally, the needle will include a circular collar that is mounted on the needle between its proximal and distal ends. More specifically, the collar will preferably be disk shaped and will extend radially from the axis of the hypodermic needle.

In detail, the connector of the present invention includes a fluid transfer section that is formed with a fluid chamber that has an input port and an output port. A septum, that is preferably made of an elastomeric material, is used to cover the output port and provide for fluid communication with the fluid chamber when it is penetrated. On the other hand, the input port is connected to a flexible hose that is provided to join the fluid chamber of the transfer section in fluid communication with the fluid medicament reservoir.

The needle holder that is used for the present invention can generally have either of three embodiments. In one embodiment, the holder is positioned in the interior of the housing and it is substantially cylindrical-shaped. It will also define at least three separate stations and, as the holder is rotated inside the housing, it will assume three different operational orientations. Specifically, during a rotation, each station will sequentially move from a position where it retrieves a sterile needle from the magazine, to a second position where the needle is presented for engagement with the connector, and then to a third position where the used needle is placed in storage. In another embodiment, the holder is positioned inside the housing to move a sterile needle along predetermined paths. Specifically, this involves moving a needle from the magazine, along a first path, and into a position for engagement with the connector. After the needle has been used, the holder then moves the needle along a second path to a storage location inside the housing. With this embodiment, the holder sequentially handles each needle individually. In yet another embodiment, the holder can be a cassette that is pre-loaded with a plurality of needles. The cassette can then be loaded onto the housing and rotated to sequentially position a needle for engagement with the connector.

In operation, the user of the auto-injector (i.e. patient) positions the housing of the auto-injector against his/her body at the desired injection site. The user then pushes a button and waits a few seconds while the injection is performed. The housing is then removed from the injection site. At no time does the user see a needle during this operation.

Inside the housing, before the user pushes the button to initiate operation of the auto-injector, the needle holder positions a sterile needle at a location in the housing for engagement with the fluid transfer section of the connector. Once the needle is so positioned, the user pushes the button to initiate operation and the drive mechanism releases a drive rod that is accelerated into contact with the fluid transfer section. The consequent transfer of momentum causes the proximal end of the needle to penetrate through the septum of the transfer section to establish fluid communication between the needle and the fluid reservoir. Further, in addition to the momentum that is transferred from the drive mechanism, forces from the drive rod can also cause the needle to be inserted into the patient for performing the injection. Once the needle is inserted into the patient (user), a plunger is advanced into the fluid reservoir to expel a dose of fluid medicament therefrom through the connector and needle, and into the patient. The needle is then subsequently withdrawn from the patient (user) and is moved by the needle holder for storage. At this point, another needle can be positioned at the location for another injection operation.

It is to be appreciated that the collar on the needle can be caused to interact with the housing during an operation of the auto-injector to limit the depth to which the needle will penetrate into the patient (user). It is also to be appreciated that the auto-injector of the present invention may include a vacuum system that can be activated to stabilize the skin of the patient at the injection site, to thereby provide for a more predictable injection.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3 is a perspective view of a needle in accordance with the present invention;

FIG. 4 is a top plan view of an embodiment of a needle holder for use with the present invention;

FIG. 5 is a top plan view of an alternate embodiment of a needle holder for use with the present invention;

FIG. 6 is a perspective view of another alternate embodiment of a needle holder for use with the present invention;

DESCRIPTION OF THE PREFERRED EMBODIMENTS

Figure 1:
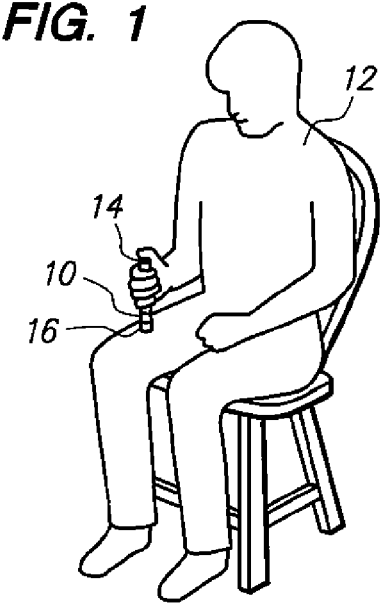
FIG. 1 is a view of a patient using an auto-injector in accordance with the present invention.

Referring initially to FIG. 1, an auto-injector 10 in accordance with the present invention is shown being used by a patient (user) 12 for a self-administration of a fluid medicament. As can be seen in FIG. 1, the auto-injector 10 includes a push-button 14 that extends from the external housing 16 of the auto-injector 10 to be depressed by the user 12 to initiate an injection. As envisioned for the present invention, all of the operational components of the auto-injector 10 are maintained out-of-sight, inside the housing 16.

Figure 2:
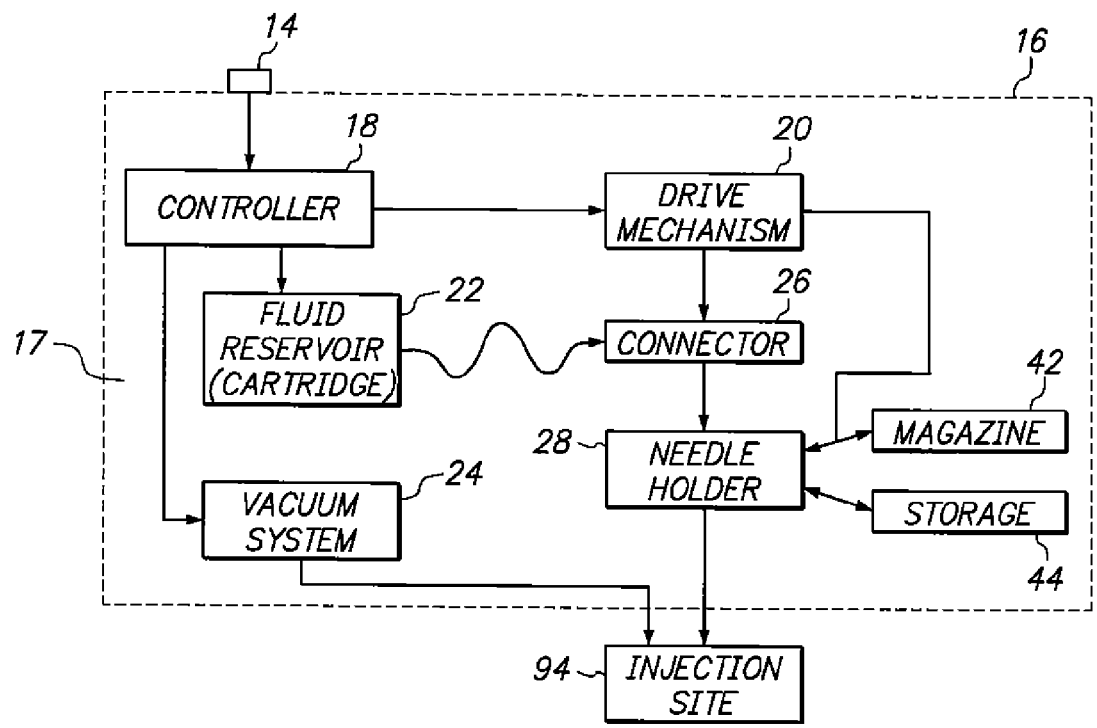
FIG. 2 is a schematic diagram of the operational components of the auto-injector of the present invention.

Referring now to FIG. 2 it will be seen that the internal components located in the interior 17 of the housing 16 of the auto-injector 10 include a controller 18 that is connected with the push-button 14. In turn, the controller 18 is connected to a drive mechanism 20, to a fluid reservoir (e.g. a fluid medicament cartridge) 22 and, optionally, to a vacuum system 24.

As envisioned by the present invention, the controller 18 may be an electronic micro-computer of a type well known in the pertinent art. In any event, the purpose of the controller 18 is to coordinate the respective operations of the drive mechanism 20, the fluid reservoir 22, the vacuum system 24 and the needle holder 28.

FIG. 2 also shows that the drive mechanism 20 is directly involved with the operations of a connector 26 and a needle holder 28. To understand the structure and inter-cooperation of these components, however, it is necessary to structurally understand the needle unit (i.e. needle) 30 that is to be manipulated by these components. For this purpose, refer to FIG. 3. There it will be seen that a needle unit 30 includes an elongated, hollow hypodermic tube 32 that has a sharp proximal end 34 and a sharp distal end 36. Further, the needle unit 30 also includes a collar 38 that is positioned and affixed on the tube 32 intermediate the ends 34 and 36. More specifically, the collar 38 is generally disk-shaped, and it extends in a radial direction from the axis that is defined by the hypodermic tube 32. FIG. 3 also shows that the distal end 36 of the tube 32 is located at a distance "l" from the collar 38.

In FIG. 4 an embodiment of the needle holder 28 is shown, and is generally designated 40. This particular embodiment 40 of the needle holder 28 is provided to move a needle unit 30 from a magazine 42, and to then subsequently move it to a storage location 44. To do this, the embodiment 40 includes an arm 46 that rotates about a point 47. A grip 48 is located at one end of the arm 46. Thus, as the arm 46 is rotated back and forth in the direction of the arrows 50, the grip 48 can, in sequence, retrieve a needle unit 30 from the magazine 42 and then move it along a path 52 to a location (shown as needle unit 30'). At this location, the needle unit 30' is positioned to cooperate with the connector 26. After its cooperation with the connector 26, needle unit 30' is then moved by the grip 48 along a path 54 to the storage location 44 (i.e. needle unit 30") where it will be stored for subsequent disposal.

FIG. 5 shows another embodiment of the needle holder 28 that is generally designated 56. For the embodiment 56 of the needle holder 28, a carousel 58 is employed to move the needle unit 30 into location for cooperation with the connector 26. More specifically, for the embodiment 56 a needle unit 30 is retrieved from the magazine 42 and moved along path 52 onto the carousel 58. The carousel 58 then rotates in the direction of the arrow 60 to the location of needle unit 30' where it cooperates with the connector 26 (see FIG. 7). After its cooperation with the connector 267 the needle unit 30' is then moved by the carousel 58 for further movement along a path 54 to the storage location 44 (shown as needle unit 30"). There it will be stored for subsequent disposal.

In FIG. 6, a cassette 61 is shown as yet another embodiment of the needle holder 28. Specifically, the cassette 61 is generally cylindrical shaped, as shown, and it is formed with a plurality of receptacles 63. As intended for the present invention, individual needle units 30 can be pre-loaded into respective receptacles 63 of the cassette 61, prior to engaging the cassette 61 with the housing 16. When used, the cassette 61 is rotated about the axis 65 to present an individual needle unit 30 at the location for cooperation with the connector 26. Thus, the cassette 61 effectively combines the functionality of the needle holder 28, the magazine 42 and the storage 44 into a single structure. It is to be appreciated that all of the embodiments of the needle holder 28 (i.e. embodiments 40 and 56, as well as cassette 61) are unitary components of the auto-injector 10. As such, they can be selectively engaged with the auto-injector 10 and, along with the spent needle units 30, individually disposed of after they have been used.

Figure 7:
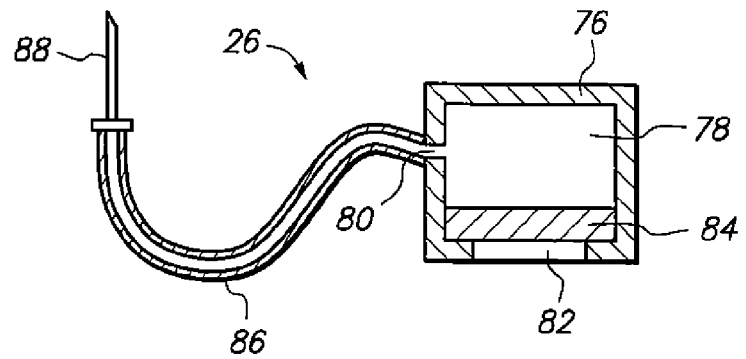
FIG. 7 is a cross-section view of a connector for use with the present invention.
Figure 8A:
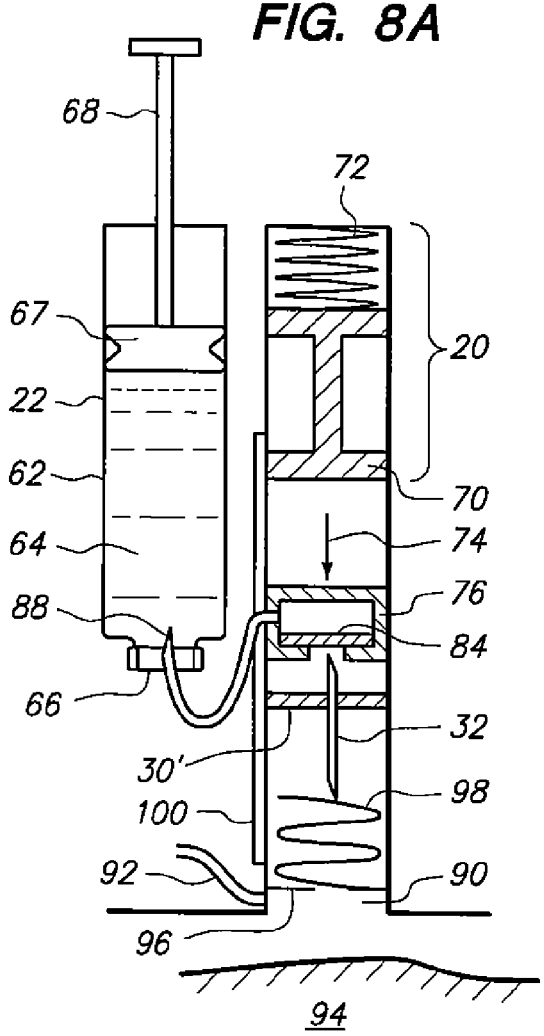
FIG. 8A is an elevation view of the drive mechanism, needle and connector, in combination with the fluid reservoir of the present invention (with portions shown in cross-section for clarity) prior to an injection.

Respective structures for the fluid reservoir 22, for the drive mechanism 20, and for the connector 26 will be best appreciated with reference to both FIG. 7 and FIG. 8A. Considering the fluid reservoir 22 first, it will be seen that the reservoir 22 includes a vial 62 for holding a fluid medicament 64 therein. A septum 66, at one end of the vial 62, is provided to establish fluid communication with the reservoir 22 whenever it (i.e. the septum 66) is penetrated. It will be appreciated, however, that any other mechanism well known in the pertinent art for establishing a fluid connection can be used for this purpose, such as a Luer fitting. The fluid reservoir 22 also includes a bung 67 that can be advanced by a plunger 68 into the vial 62 for purposes of expelling fluid medicament 64 from the reservoir 22 through a penetrated septum 66. As envisioned for the present invention, the fluid reservoir 22 can be a pre-filled cartridge that can hold either one, or multiple doses of the fluid medicament 64. Further, the plunger 68 can be calibrated to establish a specific dosage of fluid medicament 64, each time it advances the bung 67.

The drive mechanism 20 for the auto-injector 10 is shown in FIG. 8A to include a drive rod 70 that is selectively propelled by a compressed spring 72 in a linear direction indicated by the arrow 74. It will be appreciated by the skilled artisan that the actual mechanism for propelling the drive rod 70 can vary. In this context, the spring 72 is only exemplary. It is important for the present invention, however, that the propulsion of the drive rod 70 by the drive mechanism 20 develops a predetermined momentum for the drive rod 70 (see OPERATION below).

Referring specifically to FIG. 7, it will be seen that the connector 26 includes a fluid transfer section 76 that is formed with a fluid chamber 78. Further, the fluid transfer section 76 has an input port 80 to the fluid chamber 78, and it has an output port 82 that is covered by a septum 84. FIG. 7 also shows that the connector 26 includes a flex hose 86 that has one end connected for fluid communication with the input port 80 of the fluid transfer section 76. As also shown, the other end of the flex hose 86 is fitted with a spike 88 that can be used to penetrate the septum 66 of the fluid reservoir 22. For another aspect of the present invention, FIG. 8A shows that the housing 16 of auto-injector 10 can be formed with a vacuum depression 90 that is placed in fluid communication with the vacuum system 24 (see FIG. 2) via a vacuum hose 92.

OPERATION

In the operation of the auto-injector 10 of the present invention, after setting a desired dose of the fluid medicament 64 to be delivered, the user (patient) 12 will position the housing 16 against an injection site 94. The user 12 then depresses the push-button 14. After a predetermined time interval, the user 12 removes the auto-injector 10 from the injection site 94, and the injection of fluid medicament 64 into the user (patient) 12 has been completed. At no time, either before, during or after an injection, is any part of a needle unit 30 ever visible to the user 12. Furthermore, other than an earlier loading of the fluid reservoir 22, engaging the reservoir 22 with connector 26, and loading a magazine 42 of needle units 30, only a dose setting may be required before the auto-injector 10 is used. There is nothing for the user 12 to do after the injection has been completed except, perhaps, to put a cover (not shown) over the housing 16.

Referring back to FIG. 2, it will be appreciated that as the user 12 depresses the push-button 14, several mechanisms inside the housing 16 are sequentially activated by the controller 18. For one, the needle holder 28 (with either embodiment 40 or, alternatively, embodiment 56) retrieves a needle unit 30 from the magazine 42. The needle holder 28 then moves the needle unit 30 into the position indicated in the drawings as needle unit 30' (see FIG. 8A in particular). Prior to this, the connector 26 has been connected in fluid communication with the fluid reservoir 22. Specifically, this connection is made by inserting the spike 88 on flex hose 86 through the septum 66. At this point, with the needle unit 30' in position, the drive mechanism 20 comes into play.

It is an important aspect of the operation of the auto-injector 10 of the present invention, that the drive mechanism 20 propels the drive rod 70 toward the connector 26 (e.g. fluid transfer section 76) with a predetermined momentum. Specifically, in accordance with well known impulse and momentum considerations, this predetermined momentum will be determined by the mass of the drive rod 70 and its velocity (predetermined momentum=$m_{rod}v_{rod}$). As intended for the present invention, when the drive rod 70 impacts with the connector 26, its momentum ($m_{rod}v_{rod}$) is then transferred to the fluid transfer section 76 of the connector 26. Note: the flex hose 86 mechanically isolates the transfer of momentum to only the fluid transfer section 76. This transfer of momentum will then immediately accomplish several functions. For one, part of the momentum is used to establish fluid communication between the fluid transfer section 76 of the connector 26 and the needle unit 30. This is accomplished as the proximal end 34 of the hypodermic tube 32 penetrates through the septum 84. The remaining momentum that is now determined by the velocity ($v_f$) of the combined mass ($m_{combined}$) of the fluid transfer section 76 and the needle unit 30. Importantly, the velocity term ($v_f$) of this remaining momentum must be sufficient to cause the distal end 36 of the needle unit 30 to penetrate into the user (patient) 12 at the injection site 94 (see FIG. 8B). As appreciated by the present invention, the velocity that is necessary for generating the necessary predetermined momentum of the drive rod 70 need not result in an excessively high velocity for the needle unit 30. To the contrary, the intent here is to generate a so-called "light touch" that will guarantee only that an effective penetration of the needle unit 30 is achieved. A benefit here is that the possibility of creating pain or bruising at the injection site 94 is minimized. Additional benefits are that by minimizing the final momentum there is less shock to the user 12, due to reduced recoil, and there is a reduced need for energy input.

Once the needle unit 30 has penetrated the user (patient) 12 at the injection site 94, the controller 18 will then activate the fluid reservoir 22. Specifically, with this activation, the bung 67 is advanced into the vial 62 to expel fluid medicament 64 into the injection site 94. When doing this, the fluid medicament 64 traverses the flex hose 86, and enters the hypodermic tube 32 of needle unit 30 through the fluid transfer section 76. Once the injection has been completed, the needle unit 30 is withdrawn from the injection site 94. The needle holder 28 then moves the needle unit 30 to storage 44. At this point, the auto-injector 10 is rearmed and another cycle can then be performed. Once the magazine 42 is empty of needle units 30, it can be disposed of. Likewise, when the fluid reservoir 22 has been emptied of fluid medicament 64, it is ready for disposal. In some instances it may also be desirable to dispose of the connector 26.

Further to the above disclosure, it will be appreciated that the vacuum system 24 can be activated during a use of the auto-injector 10 to help stabilize the auto-injector 10 at the injection site 94 and avoid tissue compression. Specifically, when a partial vacuum is created in the vacuum depression 90 that is established as housing 16 is positioned against the injection site 94, skin from the user (patient) 12 will be drawn into the depression 90 (see FIG. 8B). This will help stabilize the auto-injector 10 during an injection without the need to push the auto-injector 10 against the skin and, thereby, compress tissue. Further, the depth to which the distal end 36 of needle unit 30 will penetrate into the user (patient) 12 can be controlled, and varied as desired. In general, penetration depths of up to around one and a half inches are considered typical. In each case, a precise penetration depth is achieved by establishing the distance "l" between the collar 38 and distal end 36 of the needle unit 30 (see FIG. 3). More specifically, this distance "l" of needle unit 30, and the location of an adjustable abutment 96 on the housing 16 will establish a travel limit for the collar 38 and needle unit 30. Consequently, a precise penetration depth can be established for the hypodermic tube 32 of the needle unit 30.

Referring again to FIG. 8A, it will be seen that the auto-injector 10 includes a recoil mechanism 98, such as a spring, that is positioned on the abutment 96 substantially as shown. FIG. 8A also shows that the auto-injector 10 includes a cocking mechanism 100 that responds to instructions from the controller 18 and is used to rearm the auto-injector 10 in preparation for a subsequent injection cycle. In operation, the recoil mechanism 98 and the cocking mechanism 100 interact with the needle unit 30 in different ways. These different operations are, perhaps, best appreciated by first considering FIG. 8B.

Figure 8B:
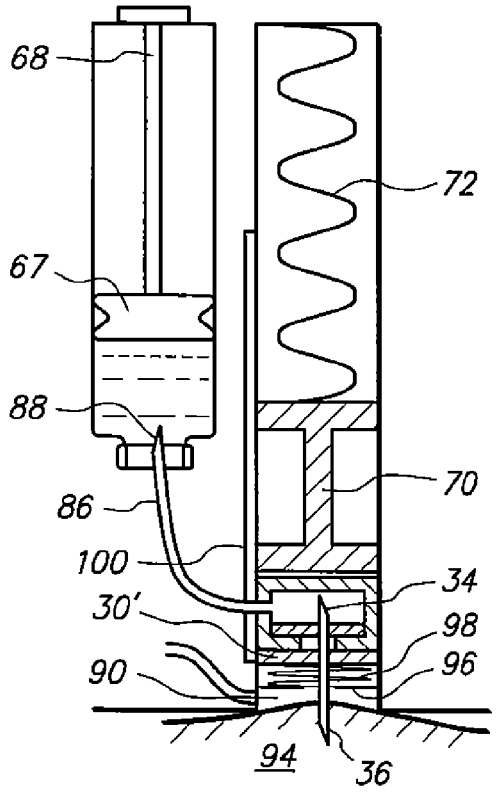
FIG. 8B is an elevation view of the same components shown in FIG. 8A during an injection.

With reference to FIG. 8B it will be seen that during an injection (i.e. after an injection cycle has been started) the spring 98 is depressed between the abutment 96 and the collar 38 of needle unit 30 (30'). While it is depressed, the spring 98 reacts against the force that is being applied by the drive spring 72 and by the drive rod 70. The depressed spring 98, however, does not overcome the combined forces that are applied by spring 72 and drive rod 70. Therefore, during an injection, the distal end 36 of needle unit 30 remains inserted at the injection site 94. Indeed, it may be desirable for the distal end 36 to remain inserted at the injection site 94, even after the injection of fluid medicament 64 is completed. If so, the controller 18 can be programmed to delay the activation of cocking mechanism 100 for the withdrawal of the distal end 36 of needle unit 30 from the injection site 94. This delay can be for any predetermined period of time (e.g. five seconds).

As indicated above, the cocking mechanism 100 is used to return the drive rod 70 and its drive spring 72 from their respective positions shown in FIG. 8B (i.e. during an injection) to those shown in FIG. 8A (i.e. preparatory to an injection). It also happens that this action returns the fluid transfer section 76 and the needle unit 30 to their positions shown in FIG. 8A. To help insure that this withdrawal is accomplished without complication, the depressed spring 98 assists in lifting the distal end 36 of needle unit 30 from the injection site 94. The needle unit 30 can then be separated from the fluid transfer section 76. Importantly, the now-used needle unit 30 can be removed from its location between the fluid transfer section 76 and the abutment 96, and replaced with a new sterile needle unit 30. The sequence of operation can then be repeated, until the supply of needle units 30 that has been loaded into the auto-injector 10 is exhausted.

While the particular Injection System with Hidden Needles as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An auto-injector for injecting a fluid into a patient which comprises:
   a housing formed with an interior;
   a fluid reservoir mounted on said housing;
   at least one needle held in the interior of said housing, wherein each needle has a sharp proximal end and a sharp distal end;
   a means mounted in the interior of said housing for positioning a needle at a location therein;
   a fluid transfer section formed with a fluid chamber and mounted in the interior of said housing, the fluid chamber having an input port and an output port, wherein said input port is in fluid communication with the fluid reservoir, and wherein a septum covers the output port;
   a flexible hose connected to said input port and to said fluid reservoir to establish fluid communication between said fluid reservoir and the fluid chamber of said transfer section; and
   a means mounted in the interior of said housing for moving the fluid transfer section from a position wherein the needle is at a distance from the fluid transfer section to the location of the needle where the septum is pierced with the sharp proximal end of the needle, and to position the proximal end of the needle in the fluid chamber to establish fluid communication between the fluid reservoir and the needle, and for thereafter moving the needle with the fluid transfer section from the location to extend the sharp distal end of the needle outside said housing for insertion into the patient to inject the fluid into the patient, wherein said fluid reservoir remains stationary while said needle moves relative to the fluid reservoir from the location into the patient.

2. An auto-injector as recited in claim 1 wherein a needle for use in the auto-injector comprises:
   an elongated hypodermic needle defining an axis and having a proximal end and a distal end; and
   a collar mounted on said hypodermic needle between the proximal end and the distal end thereof, with said collar extending radially outward therefrom for contact with said fluid transfer section to limit axial movement of the needle in a proximal direction relative to said transfer section during insertion of the proximal end of the needle through the septum and into the fluid chamber thereof, and for contact with said housing to limit axial movement of the needle in a distal direction relative to said housing during insertion of the distal end of the needle into the patient.

3. An auto-injector as recited in claim 1 wherein said moving means comprises:
   a drive rod mounted in the interior of said housing; and
   a means for accelerating said drive rod into contact with an engaging means to connect the needle with said engaging means.

4. An auto-injector as recited in claim 1 wherein said positioning means is a holder mounted in the interior of said housing for movement into an orientation with a first station positioned to retrieve a sterile needle, with a second station positioned to present a sterile needle at the location for engagement of the needle in fluid communication with said fluid reservoir, and with a third station positioned for removal of a used needle from said holder for storage.

5. An auto-injector as recited in claim 1 wherein said positioning means is a holder mounted in the interior of said housing for movement along a first path to retrieve a sterile needle for placement of the needle at the location where fluid communication is established between the needle and the fluid reservoir, and for movement along a second path to deposit the needle, after use, for storage in the interior of said housing.

6. A system for injecting a fluid into a patient which comprises:
   a housing formed with an interior;
   a fluid reservoir mounted on said housing;
   a magazine mounted on said housing for holding at least one needle;
   a means mounted in the interior of said housing for moving a needle of said magazine to a location for fluid communication engagement with said fluid reservoir, with said needle having a sharp proximal end and a sharp distal end;
   a fluid transfer section formed with a fluid chamber and mounted in the interior of said housing for movement relative to the needle, the fluid chamber having an input port and an output port, wherein said input port is in fluid communication with the fluid reservoir, and wherein a septum covers the output port;
   a flexible hose connected to said input port and to said fluid reservoir to establish fluid communication between said fluid reservoir and the fluid chamber of said transfer section; and
   a drive mechanism mounted inside said housing to drive the fluid transfer section from a position wherein the needle is at a distance from the fluid transfer section to the location of the needle and into contact with the needle to pierce the septum with the sharp proximal end of the needle, to position the proximal end of the needle in the fluid chamber of the fluid transfer section to establish fluid communication between the needle and the fluid reservoir, and to thereafter accelerate the needle with the fluid transfer section from the location for insertion of the sharp distal end of the needle into the patient, wherein said fluid reservoir remains stationary while said needle moves relative to the fluid reservoir from the location into the patient; and
   a plunger mounted inside said housing for ejecting fluid from said fluid reservoir and through said needle into the patient after said needle is moved into the patient.

7. A system as recited in claim 6 wherein said moving means is a cassette formed to hold a plurality of said needles, said cassette being moveable in the interior of said housing to sequentially present a needle at the location.

8. A system as recited in claim 6 further comprising a vacuum system for stabilizing the skin of the patient at an injection site during an injection.

9. A system as recited in claim 6 wherein a needle for use in the system comprises:
   an elongated hypodermic needle defining an axis; and
   a collar mounted on said hypodermic needle between the proximal end and the distal end thereof, with said collar extending radially outward therefrom for contact with said transfer section to limit proximal movement of the needle relative to said transfer section during insertion of the proximal end of the needle through the septum and into the fluid chamber thereof, and for contact with said housing to limit distal movement of the needle relative to said housing during insertion of the distal end of the needle into the patient.

10. A system for injecting a fluid into a patient which comprises:
    a housing formed with an interior;
    a fluid reservoir mounted on said housing;
    a magazine mounted on said housing for holding at least one needle;

a means for moving a needle of said magazine to a location, wherein the needle has a mass ($m_{needle}$) and a sharp proximal end and a sharp distal end;

a fluid transfer section formed with a fluid chamber and mounted in the interior of said housing for movement relative to the needle, the fluid chamber having an input port and an output port, wherein said input port is in fluid communication with the fluid reservoir, and wherein a septum covers the output port;

a flexible hose connected to said input port and to said fluid reservoir to establish fluid communication between said fluid reservoir and the fluid chamber of said transfer section and to mechanically isolate the fluid transfer section and the septum from the fluid reservoir;

a drive means mounted in the interior of said housing for accelerating a drive rod with a mass ($m_{rod}$) to a velocity ($v_{rod}$) to push the fluid transfer section from a position wherein the needle is at a distance from the fluid transfer section to the location of the needle and into contact with the needle with a predetermined momentum ($m_{rod}v_{rod}$), to pierce the septum with the sharp proximal end of the needle, to position the proximal end of the needle in the fluid chamber of the fluid transfer section to establish fluid communication between the fluid reservoir and the needle, and to transfer momentum from the drive rod to the needle and fluid transfer section for insertion of the sharp distal end of the needle into the patient, wherein said fluid reservoir remains stationary relative to the fluid reservoir while said needle is inserted into the patient; and a plunger mounted in the interior of said housing for ejecting fluid from said fluid reservoir and through said needle into the patient after said needle is inserted into the patient.

11. A system as recited in claim 10 wherein the mass of the drive rod is much greater than the mass of the needle ($m_{rod} \gg m_{needle}$).

12. A system as recited in claim 11 wherein the needle, the fluid transfer section, and the septum have a combined mass ($m_{combined}$).

13. A system as recited in claim 12 wherein the predetermined momentum results in a final velocity ($v_f$) for the needle wherein ($m_{rod}v_{rod}$) is substantially equal to $m_{combined}v_f$.

14. A housing with a system mounted thereon for injecting a fluid medicament into a patient, said system comprising:

an elongated hypodermic needle defining an axis and having a sharp proximal end and a sharp distal end;

a fluid reservoir mounted on the housing;

a fluid transfer section formed with a fluid chamber and positioned for movement along a pathway inside the housing, said fluid chamber having an input port and an output port, wherein a septum covers the output port;

a flexible hose interconnecting the input port of the transfer section with the fluid reservoir to establish fluid communication between the fluid reservoir and the needle;

a collar mounted on the hypodermic needle between the proximal end and the distal end thereof with the collar extending radially outward from the needle, wherein the collar limits travel of the needle along the pathway inside the housing between a first position wherein the proximal end of the needle is at a distance from the fluid transfer section and a second position wherein the sharp proximal end of the needle is engaged in fluid communication with the fluid reservoir and the sharp distal end of the needle is inserted into the patient for infusion of the fluid medicament from the reservoir to the patient while said fluid reservoir remains stationary relative to movement of the fluid transfer section; and a means for driving the fluid transfer section into contact with the needle at the first position to pierce the septum with the needle and to position the sharp proximal end of the needle in the chamber of the fluid transfer section when the collar abuts against the fluid transfer section to establish fluid communication between the needle and the fluid source, and for moving the needle from the first position to the second position.

15. A system as recited in claim 14 wherein the proximal end of the needle is sharp and the distal end of the needle is sharp.

16. A system as recited in claim 14 further comprising an abutment formed on the housing for contact with the collar to limit axial movement of the needle in a distal direction relative to the housing during insertion of the distal end of the needle into the patient.

17. A system as recited in claim 16 further comprising a recoil mechanism mounted on the abutment for engagement with the collar to bias the needle in a proximal direction relative to the housing for subsequent withdrawal of the needle from the patient when the needle is in its second position.

18. A system as recited in claim 17 wherein the recoil mechanism is a spring.

19. A system as recited in claim 14 wherein the needle and the collar, in combination, establish a needle unit, and wherein the system incorporates a plurality of needle units and the system further comprises a holder mounted on the housing to sequentially present each needle unit for individual travel along the pathway and to subsequently remove the needle unit from the pathway.

20. An injector which comprises:

a fluid source fixed on the injector;

an elongated hypodermic needle defining an axis and having a sharp proximal end and a sharp distal end;

a disk-shaped collar mounted on said hypodermic needle between the proximal end and the distal end thereof with the collar extending radially outward from the needle;

a fluid transfer section formed with a fluid chamber and mounted on the injector for movement relative to the needle from a position wherein the needle is at a distance from the fluid transfer section to the location of the needle to a location wherein the needle is in fluid communication with the fluid chamber, the fluid chamber having an input port and an output port, wherein said input port is in fluid communication with the fluid source, and wherein a septum covers the output port; and a means operable with the collar for simultaneously connecting the sharp proximal end of the needle in fluid communication with the fluid source by piercing the septum with the needle and positioning the proximal end of the needle in the fluid chamber of the fluid transfer section and for inserting the sharp distal end of the needle into a body for injecting fluid from the fluid source through the needle and into the body while said fluid source remains stationary relative to movement of the fluid transfer section, wherein the connecting and inserting means comprises a flexible hose interconnecting the input port of the transfer section with the fluid source to establish fluid communication between the fluid source and the needle.

21. An injector as recited in claim 20 wherein the needle and collar, in combination, are mounted on a housing and wherein the connecting and inserting means comprises:

an abutment formed on the housing for engagement with the collar to limit axial movement of the needle in a distal direction relative to the housing during insertion of the distal end of the needle into the body; and a recoil means mounted on the abutment for engagement with the collar to bias the needle in a proximal direction relative to the housing for subsequent withdrawal of the needle from the body.

22. An injector as recited in claim 21 wherein the body is a patient and the housing prevents visual contact by the patient with the needle.

* * * * *

UNITED STATES PATENT AND TRADEMARK OFFICE
CERTIFICATE OF CORRECTION

PATENT NO. : 7,618,396 B2  Page 1 of 1
APPLICATION NO. : 11/463529
DATED : November 17, 2009
INVENTOR(S) : John B. Slate, Andrew C. Barnes and Corey M. Magers It is certified that error appears in the above-identified patent and that said Letters Patent is hereby corrected as shown below:

Column 5, Line 46
DELETE
"267"
INSERT
--26--

Signed and Sealed this

Fifteenth Day of June, 2010

David J. Kappos
*Director of the United States Patent and Trademark Office*